United States Patent [19]
Fenton, Jr.

[11] Patent Number: 6,059,827
[45] Date of Patent: May 9, 2000

[54] SUTURELESS CARDIAC VALVE PROSTHESIS, AND DEVICES AND METHODS FOR IMPLANTING THEM

[75] Inventor: Paul V. Fenton, Jr., Marblehead, Mass.

[73] Assignee: Axya Medical, Inc., Beverly, Mass.

[21] Appl. No.: 09/072,524

[22] Filed: May 4, 1998

[51] Int. Cl.[7] ................................. A61F 2/24; A61F 2/02
[52] U.S. Cl. ................................. 623/2; 623/900
[58] Field of Search ................................. 623/2, 11, 900, 623/66, 1

[56] References Cited

U.S. PATENT DOCUMENTS

| | | | |
|---|---|---|---|
| 3,574,865 | 4/1971 | Hamaker | 623/2 |
| 5,549,666 | 8/1996 | Hata et al. | 623/2 |
| 5,578,076 | 11/1996 | Krueger et al. | 623/2 |
| 5,693,090 | 12/1997 | Unsworth et al. | 623/2 |
| 5,716,370 | 2/1998 | Williamson, IV et al. | 606/153 |
| 5,735,894 | 4/1998 | Krueger et al. | 623/2 |
| 5,800,531 | 9/1998 | Cosgrove et al. | 623/2 |
| 5,871,489 | 2/1999 | Ovil | 606/148 |

OTHER PUBLICATIONS

International Search Report of International Application No. PCT/US99/08010.
The History of Sulzer Carbomedics, *Sulzer Carbomedics, The Heart Valve Company*, 1996.
The Valve System, Choice Combinations, *Deknatel*, 1995.

*Primary Examiner*—David H. Willse
*Assistant Examiner*—Choon P. Koh
*Attorney, Agent, or Firm*—McDermott, Will & Emery

[57] ABSTRACT

A prosthetic cardiac valve assembly for sutureless implantation in a patient. The assembly includes a generally disk-shaped valve annulus element and one or more generally disk-shaped retainer elements. The elements are adapted for mutual engagement and for engagement with a host tissue region so as to fix a portion of the host tissue between them in a sutureless bond. Ultrasonic or thermal energy is applied to one or more of the elements to bond them together. Either the valve annulus element or the retainer element includes a plurality of projections, and the corresponding element includes a corresponding plurality of apertures for receiving the projections, thus providing for mutual physical engagement. The valve annulus element can include a plurality of valve leaflets which open and close in response to fluid pressure differentials across them. Various insertion devices for the assembly are designed to facilitate insertion of the elements in the heart through a relatively small incision. The elements can be implanted, assembled and bonded together in situ around the host tissue.

15 Claims, 3 Drawing Sheets

SUTURELESS CARDIAC VALVE PROSTHESIS, AND DEVICES AND METHODS FOR IMPLANTING THEM

FIELD OF THE INVENTION

The invention relates to prosthetic cardiac valves, and more particularly to prosthetic cardiac valves which can be implanted in a patient without sutures.

BACKGROUND OF THE INVENTION

Cardiac valve replacement may be required if the valve is prolapsed or otherwise malfunctioning. Replacement of a cardiac valve, such as, for example, the mitral or tricuspid valve, typically involves the resection of at least a portion of the diseased valve, leaving an annulus of host tissue, and the implantation of a prosthetic valve which includes a flexible ring and a plurality of leaflets mounted within the ring which are designed to open and close in response to changes in fluid pressure across them. The leaflets may be rotatable within the ring so that they can be oriented properly after the prosthesis has been implanted in the heart.

Prior art cardiac valve prostheses typically include a titanium ring and either two or three pyrolytic carbon leaflets (two if a mitral valve, three if a tricuspid valve). The ring is typically covered with a fabric cuff which promotes endothelialization of cardiac tissue into the prosthesis.

The prosthesis is generally secured to the annulus of native tissue at the valve site within the heart with a relatively large number of sutures which must be precisely placed and oriented so that the prosthesis does not rotate and the movement of the leaflets is not impeded when the prosthesis is in place. In practice, the prosthetic valve is secured to the host tissue using sutures attached to the fabric cuff surrounding the ring. Generally, relatively long sutures are passed through the tissue at the intended valve site and carefully laid out to extend through the incision in patient's chest, to points outside the incision. Then, the distal ends of the sutures are coupled to the cuff, and finally the valve and cuff are "parachuted", or slid down the sutures, into place with the orientation of the valve maintained. The sutures anchoring the cuff of the prosthesis to the host tissue are then tied off.

Open-heart surgery is complicated, delicate, and confined. Minimally invasive surgical technologies and techniques are favored to minimize patient trauma; however, such procedures require a high degree of surgical skill. The implantation of a prosthetic valve with large numbers of sutures that cannot be crossed or otherwise twisted or misplaced is painstaking and difficult and prolongs the surgical procedure, thereby increasing patient trauma and the risk of infection. It would be an advancement in the art of cardiac valve replacement surgery to provide a valve which can be implanted without sutures.

SUMMARY OF THE INVENTION

According to one aspect of the invention, there is provided a prosthetic cardiac valve assembly for sutureless implantation in a living patient. The assembly comprises a valve annulus element and at least one retainer element which are adapted for mutual engagement and engagement with one or more sections of host tissue. The valve annulus element and retainer element are made of a biocompatible material and can be bonded together around the section or sections of host tissue upon application of energy to one or more of the elements, thereby fixing the host tissue between them without sutures. Preferably, the material is a thermoplastic material which is suitable for bonding using ultrasonic or thermal welding techniques.

The valve annulus element can, but need not, include a plurality of valve leaflets which are pivotably mounted in the valve annulus element for controlling fluid flow through the assembly in response to fluid pressure differentials across the leaflets. In one embodiment, the prosthetic cardiac valve assembly is suitable for use as a mitral valve, and the valve annulus element includes a pair of valve leaflets. In another embodiment, the assembly is suitable for use as a tricuspid valve, and the valve annulus element includes three valve leaflets. The valve leaflets can be made of living tissue, such as porcine tissue, or from a synthetic material. In another embodiment, the valve annulus element contains no leaflets and is suitable for use in annuloplastic surgery.

Either or both of the retainer element and the annulus preferably include a plurality of projecting members, and the mating part includes a corresponding plurality of apertures adapted to receive the projecting members. In this embodiment, the valve annulus element is held to the retainer element by mechanical engagement of the projecting members in corresponding apertures on the mating part.

In one embodiment, the retainer element is in the form of a single-piece, continuous ring; in another embodiment the retainer is a multi-piece ring. In still another embodiment the assembly includes a pair of retainer elements, the first retainer element including a plurality of projecting members, and the second retainer element including a corresponding plurality of apertures adapted to snugly receive the projecting members of the first retainer element. In this embodiment, the valve annulus element is held frictionally between the first and second retainer elements.

At least one of the valve annulus element and the retainer element includes a tissue anchor for penetrating the host tissue and facilitating and maintaining the placement of the assembly.

The tissue-contacting surfaces of the valve annulus element and retainer element are preferably adapted to promote endothelialization of the host tissue into and around the supporting ring-like portion of the valve assembly.

The valve annulus element and the retainer element are preferably adapted to be bonded together upon application of ultrasonic or thermal energy to one or both of the elements.

According to another aspect of the invention, there is provided an insertion device for sutureless implantation of a generally disk-shaped cardiac valve prosthesis in a living patient. The device comprises a flat elongated member extending along a principal axis between distal and proximal ends. The proximal end of the device includes a handle, and the distal end includes a plurality of fingers that extend at least partially in the direction of the principal axis. The fingers are adapted to receive and hold a generally disk-shaped cardiac valve prosthesis in an orientation having its principal plane substantially parallel to the principal axis of the device during implantation of the prosthesis.

According to still another aspect of the invention, there is provided a different insertion device for sutureless implantation of a generally disk-shaped cardiac valve prosthesis in a living patient. The device comprises a plurality of rigid wires, each wire including a tissue anchor at a distal end thereof for penetrating host tissue. In use the wires are disposed parallel to each other, and each wire is engageable with a portion of the circumference of the prosthesis so that the prosthesis is supported by the wires and is maneuverable by and within the wires to various positions between and including positions transverse to and substantially parallel to the wires. The insertion device includes at least a pair of wires and may include three or more wires.

According to still another aspect of the invention, there is provided a method of implanting a generally disk-shaped cardiac valve prosthesis in a living patient without using sutures. The method comprises the steps of:

a. Providing a prosthetic cardiac valve assembly, including a valve annulus element and at least one retainer element, which elements are adapted for mutual engagement with one or more sections of host tissue;

b. Providing an insertion device for the assembly for holding and maneuvering the valve assembly;

c. Preparing the patient's chest cavity and heart to receive the assembly and the insertion device, wherein one or more sections of host tissue surrounds a valve implant region;

d. Orienting the valve annulus element of the assembly so that its principal plane is substantially parallel to the principal axis of the insertion device and inserting the valve annulus element into the valve implant region of the patient's heart so that in situ the valve annulus element is overlying and in substantial registration with the host tissue, and fixing the valve annulus element to the host tissue with the tissue anchor so as to position the valve annulus element over the valve implant region;

e. Orienting the retainer element of the assembly so that its principal plane is substantially parallel to the principal axis of the insertion device and inserting the retainer element into the valve implant region of the patient's heart so that in situ the retainer element is lying under and in substantial registration with the host tissue and with the valve annulus element, thereby sandwiching the sections of host tissue between the retainer element and the valve annulus element, and fixing the retainer element to the host tissue with the tissue anchor so as to position the retainer element in substantial registration with the valve annulus element over the valve implant region;

f. Withdrawing the insertion device from the patient's heart and chest cavity; and g. Applying energy to the assembly to fuse the retainer element and the valve annulus element together and fix the sections of host tissue between them.

In one embodiment, the insertion device comprises a flat elongated member extending along a principal axis between distal and proximal ends, the proximal end including a handle, and the distal end including a plurality of fingers extending at their distal ends in the direction of the principal axis. The fingers of the device are adapted to receive and hold a generally disk-shaped cardiac valve prosthesis in an orientation such that its principal plane is substantially parallel to the principal axis of the device during implantation of the prosthesis.

In another embodiment, the insertion device comprises a plurality of rigid wires, each wire including a tissue anchor at a distal end thereof for penetrating host tissue. Each wire is engageable with a portion of the circumference of the prosthesis so that the prosthesis is supported by the wires and is maneuverable by and within the wires to positions that include positions transverse to and substantially parallel to the wires.

One the assembly is assembled in situ and maintained in its desired orientation in the heart, ultrasonic or thermal energy can be applied to the assembly to bond the valve annulus element and retainer element or elements together around the sections of host tissue.

According to still another aspect of the invention, there is provided a method of implanting a prior art generally disk-shaped cardiac valve prosthesis in a living patient. The method comprises the steps of:

a. Providing a prosthetic cardiac valve, including a valve annulus element which is adapted to engage with a corresponding region of host tissue;

b. Providing an insertion device for holding and maneuvering the valve annulus element;

c. Preparing the patient's chest cavity and heart to receive the valve annulus element and the insertion device, wherein one or more sections of host tissue surrounds a valve implant region;

d. Orienting the valve annulus element parallel to the principal axis of the insertion device and inserting the valve annulus element into the patient's heart so that in situ the valve annulus element is in substantial registration with the host tissue, and attaching the valve annulus element to the host tissue; and e. Withdrawing the insertion device from the patient's heart and chest cavity.

The insertion device can be, for example, either of the insertion devices described above.

These and other features of the invention will be more fully appreciated with reference to the following detailed description which is to be read in conjunction with the attached drawings.

BRIEF DESCRIPTION OF THE DRAWINGS

The invention is further described by the following description and figures, in which.

Like elements in the respective FIGURES have the same reference numbers.

DETAILED DESCRIPTION OF THE PREFERRED EMBODIMENTS

The cardiac valve prosthesis of the present invention can be implanted and properly oriented in the patient's heart without sutures and, therefore, without the difficulties inherent in the use of sutures for valve placement. The prosthetic valve of the present invention is an assembly which can be implanted and assembled in situ around one or more sections, or an annulus, of host tissue using minimally invasive surgical (MIS) techniques. Ultrasonic or thermal energy is then applied to one or more of the elements of the assembly to bond them together around, and couple them to, the host tissue. Application of ultrasonic energy to the assembly in situ provides a clean and durable weld of the components without traumatizing surrounding tissue and eliminates the risk of valve misplacement due to suture crossing and entanglement. It also eliminates the requirement of suture guides for accurate placement and fixation of the prosthesis.

Figure 1:
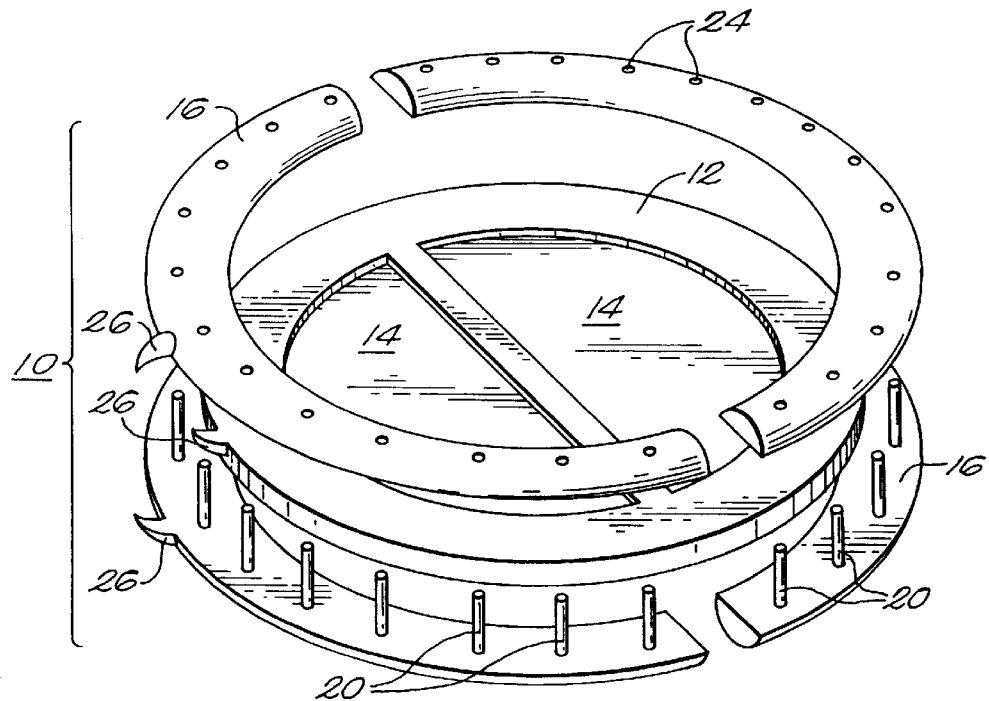
FIG. 1 is an exploded perspective view of a prosthetic valve assembly according to one embodiment of the invention.

One embodiment of the invention is illustrated in FIG. 1. According to this embodiment, the cardiac valve prosthesis 10 includes a valve annulus element 12 and at least one retainer element 16 (two are shown in the embodiment of FIG. 1, and one is shown in the embodiment of FIGS. 2 and 3), which is adapted to engage with the valve annulus element 12, as well as with a corresponding section or annulus of host tissue 18 (shown in FIGS. 4A, 4B, 5 and 8C).

The valve annulus element 12 can include a plurality of valve leaflets 14 which are pivotably mounted in the valve annulus element to control fluid flow through the valve in response to fluid pressure differentials across the valve leaflets. The valve annulus element 12 can include two valve leaflets if it is intended for use as a mitral valve prosthesis, or three leaflets if it is intended for use as a tricuspid valve prosthesis. The valve leaflets can be made of a biocompatible synthetic material, such as pyrolized carbon, which is highly resistant to clot formation, or they can be made of living tissue, such as porcine tissue, which is compatible with human tissue, as known in the art, and may have a form known in the art.

In some patients, valve replacement is not necessary. The patient's own valve is suitable for use after selected portions are resected and an annular element is implanted at the base of the valve leaflets. Such an annular element can be made in the form of a valve annulus element 12 or a retainer element 16, as shown in FIGS. 1, 2 or 3 with no value leaflets.

Figure 2:
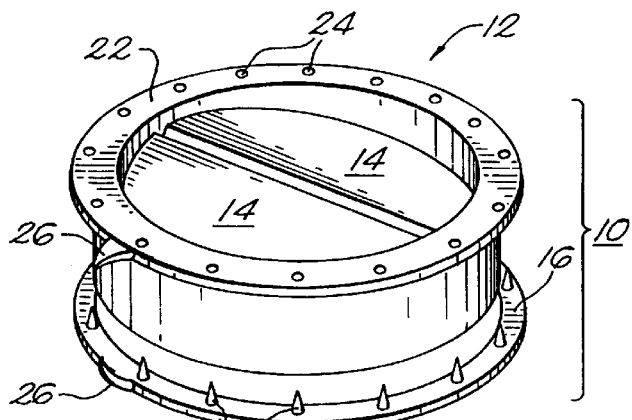
FIG. 2 is an exploded perspective view of another embodiment of the invention.
Figure 3:
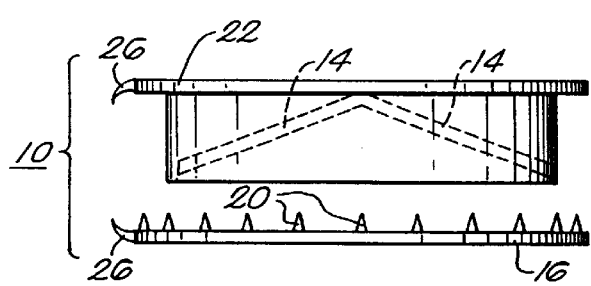
FIG. 3 is a side view of the components of a similar embodiment to that shown in FIG. 2.

FIGS. 2 and 3 illustrate another embodiment of the invention, in which a single retainer element 16 is engageable with a flanged valve annulus element 12. In both embodiments, the retainer element 16 includes projections 20 which extend toward a second retainer element 16, as in FIG. 1, or toward a flange 22 on the valve annulus element 12. The retainer element 16 and flange 22 include corresponding apertures 24 which receive the projections 20. These structures permit the valve annulus element 12 and retainer element(s) 16 to engage with each other in situ, capturing one or more sections or an annulus of host tissue between them, as detailed more fully below. The projections 20 may also act as energy directors for ultrasonic energy applied to the retainer element or valve annulus element with an ultrasonic weld horn and anvil.

In FIG. 2, the projections 20 are shown to be extending from the retainer element 16 and adapted for mating engagement with apertures in the flange 22. The respective positions of projections and apertures can, of course, be reversed in other embodiments.

The retainer element 16 can be in the form of a continuous ring which corresponds to the size of the valve annulus element, as shown in FIG. 3, or it can be in two or more separate pieces, such as a split ring, as shown in FIGS. 1 and 2. A multi-part ring may be beneficial in some circumstances, as it provides flexibility of sizing and attachment to the valve annulus element and to discrete or discontinuous sections of host tissue. A continuous ring may be beneficial in other circumstances, as it is a single piece and is easier to implant and integrate with the valve annulus element. The valve annulus element can be in the form of a split or multi-section ring as well, as needed.

At least one of the valve annulus element 12 and the retainer element(s) 16 includes a tissue anchor 26 extending outwardly from the circumference of the valve annulus element or retainer element. The tissue anchor 26 is a barb-like projection which can pierce the host tissue and hold the assembly in place temporarily until it can be properly located and oriented in the heart, as detailed more fully below.

Figure 4A:
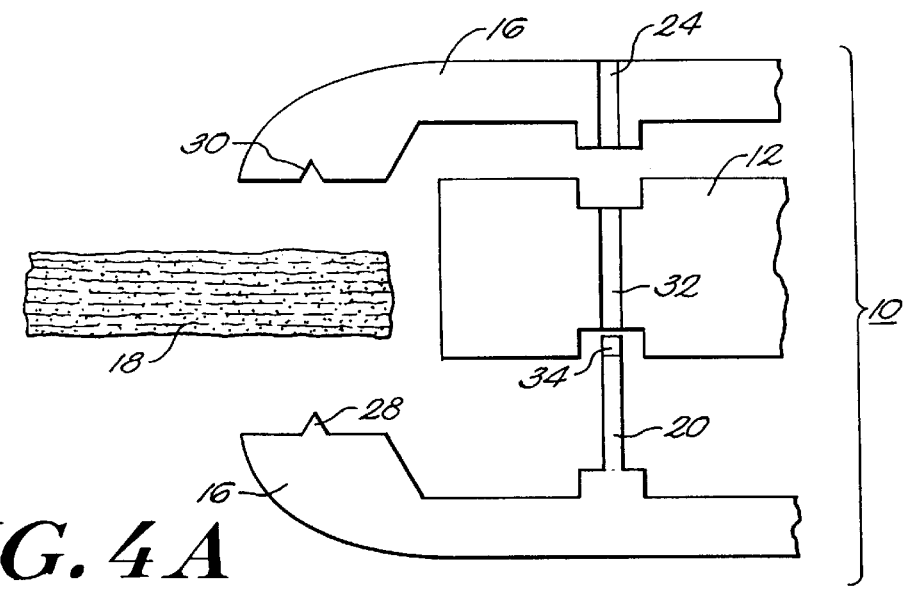
FIG. 4A is an enlarged side view of a portion of the assembly, in which the components of the assembly are in place in the heart but not assembled together.
Figure 4B:
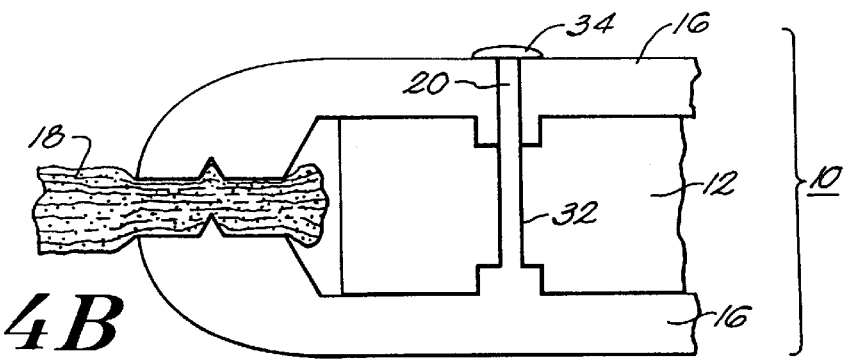
FIG. 4B is an enlarged side view of a portion of the assembly, in which the components of the assembly are assembled together around a section of host tissue within the heart.

The valve annulus element 12 and the retainer element(s) 16 are preferably made of a biocompatible material, preferably a thermoplastic material, which can be bonded or welded together around one or more sections of host tissue, as shown in FIGS. 4A and 4B, upon the application of energy, such as ultrasonic or thermal energy, to one or both of the valve annulus element and the retainer element(s). The host tissue can thus be captured and held securely and atraumatically within the valve assembly 10 without the need for sutures.

In FIG. 4A, retainer elements 16 are engaged with an annulus of host tissue 18, and tooth 28 in the lower retainer element 16 penetrates tissue 18 and fits within corresponding recess 30 in the upper opposing retainer element. The valve annulus element 12 is sandwiched between the retainer elements 16, and projection 20 (shown for convenience in shortened form in FIG. 4A) in the lower retainer element extends through a countersunk hole 32 in the valve annulus element 12 and through aperture 24 in the upper retainer element. The projection 20 includes a head portion 34 which extends beyond the top of the aperture 24 when the retainer elements are fully assembled around the valve annulus element and host tissue. Energy applied to the head portion 34 of the projection causes it to melt and flatten out over the aperture, as shown in FIG. 4B, thereby anchoring the projection in the aperture and welding the retainer elements 16 together around the valve annulus element 12 and the host tissue annulus 18.

Figure 5:
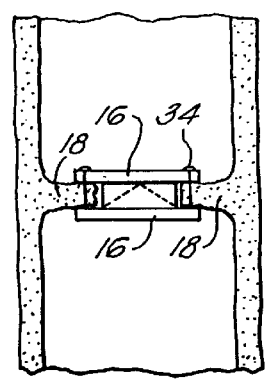
FIG. 5 is a side view of a portion of the heart showing placement of the valve assembly.

The valve assembly as implanted is shown in FIG. 5. Host tissue 18 may form an annulus or discrete portions of an annulus, into which the valve annulus elements is installed, as detailed more fully below. The retainer element(s) 16 grip opposite surfaces of the host tissue sections or annulus so that the valve annulus element 12 is held in place between them, if the embodiment of FIG. 1 (two retainer elements) is used. If the embodiment of FIGS. 2 and 3 (one retainer element) is used, the retainer element 16 and flange 22 of the valve annulus element engage opposite surfaces of the host tissue to secure the valve annulus element in place.

Figure 6:
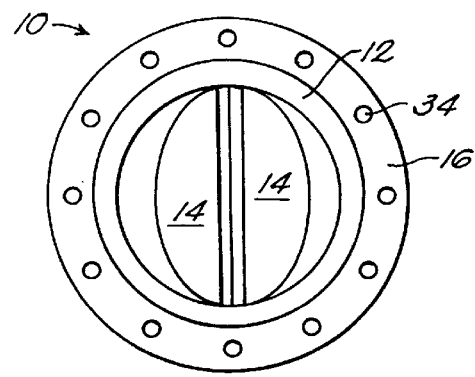
FIG. 6 is a plan view of the valve assembly.

FIG. 6 illustrates a plan view of the valve assembly. The valve leaflets 14 are freely movable within the valve annulus element 12 in response to fluid pressure differentials across them. Retainer element 16 is held in place, either attached to a complementary retainer element or to a complementary flange 22 integral with the valve annulus element, as shown in FIGS. 2 and 3. Projections 20 extend through apertures 24 in the retainer element 16 and head portion 34 is caused to flow plastically with the application of energy to form a flattened head over the aperture, thereby welding the retainer elements (or retainer element and flange of the valve annulus element) to each other around the host tissue.

Figure 7:
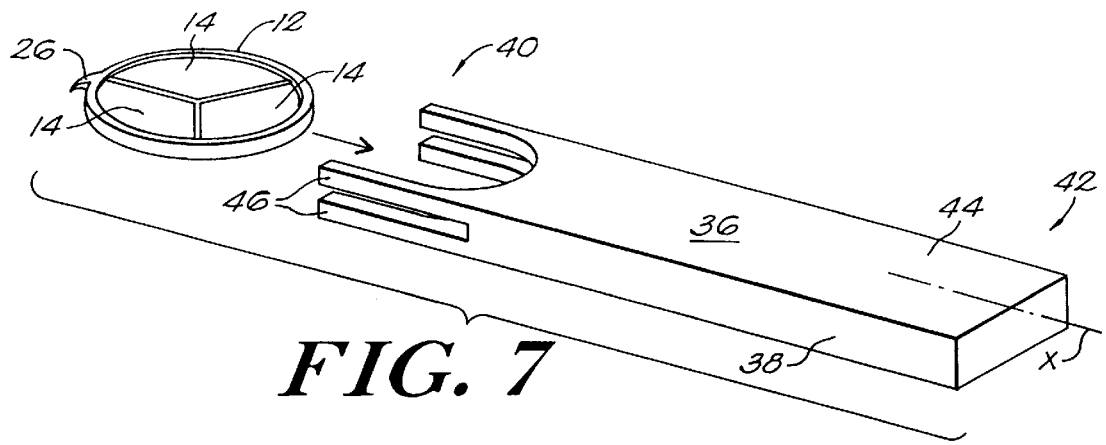
FIG. 7 is a perspective view of an insertion device for the valve assembly, which allows the assembly to be inserted into the heart through a relatively small incision in the patient's chest.

FIG. 7 illustrates one embodiment of an insertion device 36 that can be used to implant the valve assembly (illustrated here as a generally disk-shaped tricuspid valve prosthesis) in a patient through an incision in the patient's chest and heart wall. The insertion device of this embodiment comprises a flat elongated member 38 extending along a principal axis X between distal end 40 and proximal end 42. The proximal end 42 includes a handle 44 which can be shaped, sized and textured as known in the art to facilitate grasping and manipulation by a surgeon. The distal end 40 of the device includes a plurality of fingers 46 which at their distal ends can extend, for example, at least partially in the direction of the principal axis X to surround or otherwise receive and hold the complete valve assembly or its individual elements, namely, the valve annulus element and retainer element(s). The valve assembly can fit easily within the opening between the fingers 46 at the end of the insertion device and can also be easily released from the device. The insertion device maintains the valve assembly or components in an orientation in which the principal planes of the elements of the assembly are substantially parallel to the principal axis X of the device, so that the elements of the assembly and insertion device can be inserted into the patient's chest through a relatively small incision using minimally invasive surgical techniques.

The tissue anchor 26 on the valve assembly assists in orientation and location of the device in the heart and facilitates removal of the insertion device 36 from the heart by piercing the host tissue in the valve implant region and holding the valve assembly in place while the insertion device is withdrawn.

Figure 8A:
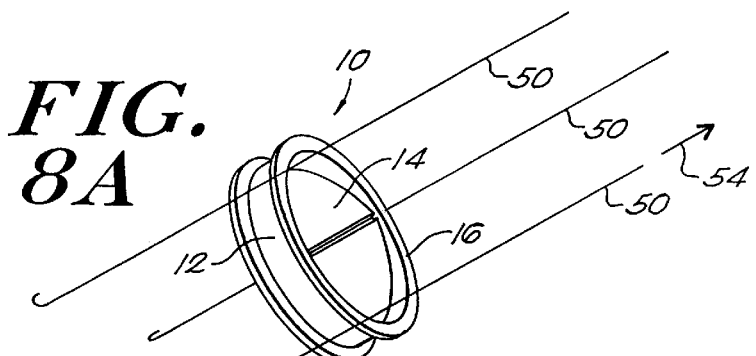
FIG. 8A is a side view of another insertion device, comprising a plurality of wires which engage with the valve assembly.
Figure 8B:
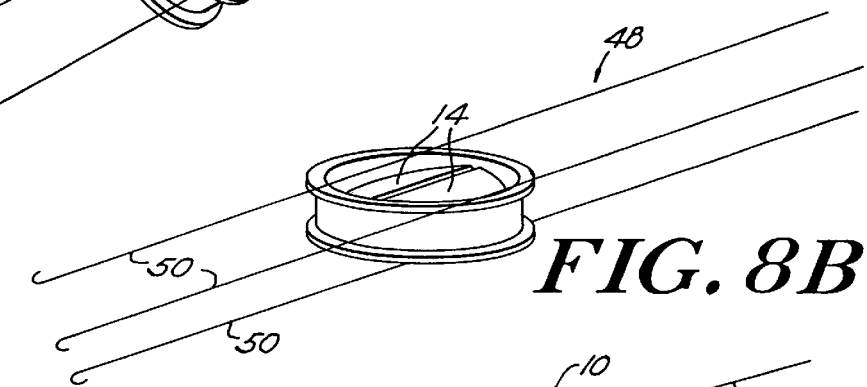
FIG. 8B is a side view of the valve assembly and insertion wires of FIG. 8A, in which the valve assembly is maneuvered to be nearly parallel to the insertion wires.
Figure 8C:
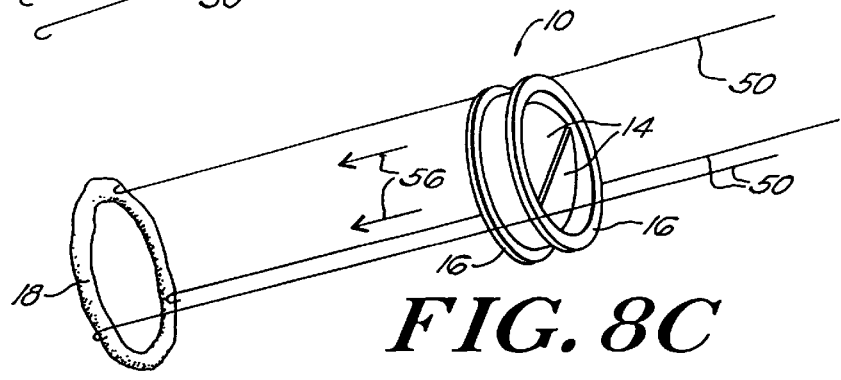
FIG. 8C is a side view of the valve assembly and insertion wires of FIGS. 8A and 8B, showing implantation of the assembly using the insertion wires.

FIGS. 8A–8C illustrate another embodiment of an insertion device 48 for the valve assembly of the invention. This insertion device comprises a plurality of rigid wires 50 which can engage with portions of the circumference of the retainer element(s) 16 and valve annulus element 12 as shown in the FIGURES. Two, three or more wires can be used, depending on available space and the degree of maneuverability required. Each of the wires includes a barb-like tissue anchor 52 at a distal end thereof which can penetrate the host tissue 18 and anchor the wires so that the valve annulus element 12 and the retainer element(s) 16 of the valve assembly can be parachuted along them into the proper location in the heart, as shown in FIG. 8C.

The wires 50 support the individual components of the valve assembly and allow them each to be oriented in a variety of positions, from a position which is substantially perpendicular to the wires, as shown in FIGS. 8A and 8C, to a position which is substantially parallel to the wires, as shown in FIG. 8B. If one of the wires in FIG. 8A is pulled in the direction of the arrow 54, the portion of the component which is engaged with that wire will be pulled in that direction, as shown in FIG. 8B, as a result of the friction between the wire and the component. This causes the generally disk-shaped component to lie along, or substantially parallel to, the wires. This orientation allows the elements to be inserted through a relatively small incision in the patient's chest and heart. Once the elements of the valve assembly are inside the heart, the wires can grasp the host tissue 18 with the tissue anchors, and the elements can be oriented as needed in preparation for final assembly and implantation in the valve implant region in the heart. The elements can then be gently urged along the wires in the direction of arrows 56 toward the annulus of host tissue 18.

A method for sutureless implantation of the valve assembly of the present invention using the insertion devices of the invention involves the orientation of the generally disk-shaped valve annulus element and retainer element(s) so that they can pass into the body through a relatively small incision in the patient's chest and heart walls. Because of the geometry of the valve implant region in the heart, and the preference for performing open-heart surgery using minimally invasive surgical techniques, it is necessary to insert each of the components of the assembly of the invention individually, one on each side of the host tissue annulus, and assemble them in situ around the host tissue section(s) or annulus. As described previously in connection with FIGS. 4A and 4B, the valve annulus element 12 and one or more retainer elements 16 are joined together around an annular or partially annular section of host tissue by ultrasonic or thermal welding.

The method comprises the steps of:

a. Providing a generally disk-shaped prosthetic cardiac valve assembly, including a valve annulus element and at least one retainer element adapted for mutual engagement with host tissue, wherein the valve annulus element and retainer element are made of a biocompatible material and can be bonded together around one or more sections of host tissue upon application of energy to the prosthesis, and wherein at least one of the valve annulus element and the retainer element includes a tissue anchor for penetrating the host tissue;

b. Providing an insertion device for the assembly for holding and maneuvering the assembly;

c. Preparing the patient's chest cavity and heart to receive the assembly and the insertion device, wherein one or more sections of host tissue surrounds a valve implant region;

d. Orienting the valve annulus element of the assembly so that its principal plane is substantially parallel to the principal axis of the insertion device and inserting the valve annulus element into the patient's heart so that in situ the valve annulus element is overlying and in substantial registration with the host tissue, and fixing the valve annulus element to the host tissue with the tissue anchor so as to position the valve annulus element over the valve implant region;

e. Orienting the retainer element of the assembly so that its principal plane is substantially parallel to the principal axis of the insertion device and inserting the retainer element into the valve implant region of the patient's heart so that in situ the retainer element is lying under and in substantial registration with the sections of host tissue and with the valve annulus element, thereby sandwiching the sections of host tissue between the retainer element and the valve annulus element, and fixing the retainer element to the host tissue with the tissue anchor so as to position the retainer element in registration with the valve annulus element over the valve implant region;

f. Withdrawing the insertion device from the patient's heart and chest cavity; and g. Applying energy to the assembly to fuse the retainer element and the valve annulus element together and fix the host tissue between them.

The method of the invention can also be used to implant a prior art generally disk-shaped cardiac valve prosthesis in a patient's heart. According to the method, a prosthetic cardiac valve a valve annulus element which is adapted to engage with a section or sections of host tissue, is provided. An insertion device for holding and maneuvering the valve annulus element is also provided. The patient's chest cavity and heart are then prepared to receive the valve annulus element and the insertion device. Typically, one or more sections of host tissue surrounds a valve implant region. The valve annulus element is oriented so that its principal plane is substantially parallel to the principal axis of the insertion device, and the valve annulus element is inserted into the patient's heart so that in situ the valve annulus element is in substantial registration with the valve opening in the host tissue. The valve annulus element is then attached to the host tissue. The insertion device is then withdrawn from the patient's heart and chest cavity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. A prosthetic cardiac valve assembly for sutureless implantation in a living patient, comprising:

a valve annulus element; and at least one retainer element, the elements being adapted for mutual engagement and engagement with a corresponding region of host tissue;

wherein the valve annulus element and retainer element are made of a biocompatible material that can be bonded together around the region of host tissue upon application of energy to one or both of the elements, thereby fixing the host tissue between them without sutures.

2. An assembly according to claim 1, wherein the valve annulus element includes a plurality of valve leaflets pivotably mounted in the valve annulus element for controlling fluid flow through the assembly in response to fluid pressure differentials across the leaflets.

3. An assembly according to claim 2, wherein the valve annulus element includes two valve leaflets.

4. An assembly according to claim 2, wherein the valve annulus element includes three valve leaflets.

5. An assembly according to claim 2, wherein the valve leaflets are made of a synthetic material.

6. An assembly according to claim 2, wherein the valve leaflets are made of living tissue.

7. An assembly according to claim 1, wherein one of the retainer element and the valve annulus element includes a plurality of projecting members, and the element not including the projecting members includes a corresponding plurality of apertures adapted to receive the projecting members of the other element.

8. An assembly according to claim 7, wherein the retainer element is in the form of one or more separate portions.

9. An assembly according to claim 1, comprising a pair of retainer elements, wherein a first retainer element includes a plurality of projecting members, and a second retainer element includes a corresponding plurality of apertures adapted to receive the projecting members of the first retainer element, and wherein the valve annulus element is held between the first and second retainer elements.

10. An assembly according to claim 9, wherein the valve annulus element includes a plurality of corresponding apertures adapted to be in substantial registration with the apertures of the second element and to receive the projecting members of the first retainer element.

11. An assembly according to claim 9, wherein the first and second retainer elements are each in the form of one or more separate portions.

12. An assembly according to claim 1, wherein at least one of the valve annulus element and the retainer element includes a tissue anchor for penetrating the host tissue.

13. An assembly according to claim 1, wherein the tissue-contacting surfaces of the valve annulus element and retainer element are adapted to promote endothelialization of the host tissue into and around the valve assembly.

14. An assembly according to claim 1, wherein the valve annulus element and retainer element are adapted to be bonded together upon application of ultrasonic energy thereto.

15. An assembly to claim 1, wherein the valve annulus element and retainer element are adapted to be bonded together upon application of thermal energy thereto.

* * * * *